United States Patent
Bae et al.

(10) Patent No.: US 8,859,265 B2
(45) Date of Patent: Oct. 14, 2014

(54) LATERAL FLOW IMMUNOASSAY DEVICE WITH A MORE RAPID AND ACCURATE TEST RESULT

(75) Inventors: Byeong-woo Bae, Anyang (KR); Bum-joo Ahn, Seoul (KR); Jj-hun Shin, Seoul (KR); Seok-Ki Lee, Incheon (KR); Jin-hee Jang, Anyang (KR)

(73) Assignee: Infopia Co., Ltd. (KR)

( * ) Notice: Subject to any disclaimer, the term of this patent is extended or adjusted under 35 U.S.C. 154(b) by 748 days.

(21) Appl. No.: 12/816,692

(22) Filed: Jun. 16, 2010

(65) Prior Publication Data
US 2011/0117636 A1 May 19, 2011

(30) Foreign Application Priority Data
Nov. 18, 2009 (KR) .......... 10-2009-0111353

(51) Int. Cl.
*C12M 1/34* (2006.01)
*C12M 3/00* (2006.01)
*G01N 33/558* (2006.01)

(52) U.S. Cl.
CPC ....... *G01N 33/558* (2013.01); *B01L 2300/0636* (2013.01); *B01J 2219/00722* (2013.01)
USPC .............................. 435/287.2; 435/5; 435/7.1

(58) Field of Classification Search
CPC .............. G01N 33/558; B01J 2219/00722; B01J 2219/00659; B01L 7/52; B01L 2300/0636; C40B 40/06
USPC .......................................... 435/5, 7.1, 287.2
See application file for complete search history.

(56) References Cited

U.S. PATENT DOCUMENTS

| 5,073,484 A | 12/1991 | Swanson et al. |
| 5,559,041 A | 9/1996 | Kang et al. |
| 5,622,871 A | 4/1997 | May et al. |
| 5,713,389 A | 2/1998 | Wilson, Jr. et al. |
| 5,728,587 A * | 3/1998 | Kang et al. ............. 436/518 |
| 6,020,147 A | 2/2000 | Guire et al. |
| 6,673,629 B2 | 1/2004 | Yoshimura et al. |
| 7,045,297 B2 | 5/2006 | Hajizadeh et al. |

(Continued)

FOREIGN PATENT DOCUMENTS

| KR | 1020010034165 A | 4/2001 | |
| KR | 1020050046265 A | 5/2005 | |
| KR | 1020060109595 A * | 10/2006 | .............. G01N 33/53 |

OTHER PUBLICATIONS

Machine translation of KR1020060109595 A (translated on May 24, 2011).*

(Continued)

*Primary Examiner* — Michael Hobbs
(74) *Attorney, Agent, or Firm* — Cantor Colburn LLP

(57) ABSTRACT

The present invention provides a lateral flow immunoassay device for qualitative or quantitative analysis of an analyte of interest in a whole blood sample with a more rapid and accurate result. This device includes a sample receiving pad, a conjugate pad, a flow delaying pad and a wicking membrane in this order. A polycation is provided within and bound to the sample receiving pad in order to separate the red blood cell from the whole blood sample. A relation between average pore size (P1) of the sample receiving pad, average pore size (P2) of the conjugate pad, and average pore size (P3) of the flow delaying pad is as follows: P1>P2>P3.

11 Claims, 1 Drawing Sheet

(56) References Cited

U.S. PATENT DOCUMENTS

| | | |
|---|---|---|
| 7,109,942 B2 | 9/2006 | McCarville et al. |
| 7,371,582 B2 | 5/2008 | Nahm et al. |
| 2001/0006823 A1* | 7/2001 | Yoshimura et al. ........... 436/518 |
| 2002/0187510 A1* | 12/2002 | Tachikawa et al. ............ 435/7.1 |
| 2006/0024767 A1* | 2/2006 | Hajizadeh et al. ........... 435/7.92 |
| 2007/0020768 A1 | 1/2007 | Rundstrom et al. |
| 2009/0253119 A1* | 10/2009 | Zhou et al. ........................ 435/5 |

OTHER PUBLICATIONS

English translated "Comparisons Between the Present Invention and the Cited References" submitted in Korean Patent Application No. 10-2009-0111353.

\* cited by examiner

LATERAL FLOW IMMUNOASSAY DEVICE WITH A MORE RAPID AND ACCURATE TEST RESULT

FIELD OF THE INVENTION

The present invention generally relates to a lateral flow immunoassay device for qualitative or quantitative analysis of an analyte of interest in a whole blood sample with a more rapid and accurate result.

In particular, the present invention relates to analytical devices which are suitable for use in the home, clinic or doctor's surgery and which are intended to give an analytical result which is rapid and which requires the minimum degree of skill and involvement from the user.

BACKGROUND OF THE INVENTION

Various methods for detecting the presence of an analyte in a sample of biological fluid through the use of immunochemistry have been described. In the so-called "sandwich" method, for example, a target analyte such as an antigen is "sandwiched" between a labeled antibody and an antibody immobilized onto a solid capillary support. The assay is read by observing the presence and amount of bound antigen-labeled antibody complex. Because such a method discussed below can detect both antibodies and antigens, they are generally referred to as immunochemical antigen-antibody assays or simply binding ligand affinity assay.

Solid phase immunoassay devices provide sensitive detection of an analyte in a biological fluid sample such as a whole blood sample. Solid phase immunoassay devices incorporate a solid capillary support to which one member of a ligand-receptor pair, usually an antibody, antigen, nucleic acid aptamer or hapten, is bound. Common early forms of solid capillary supports were plates, tubes, or beads of polystyrene which were well known from the fields of radio isotopic immunoassay and enzyme immunoassay. More recently, a number of porous materials such as nylon, nitrocellulose, cellulose acetate, glass fibers, PVDF (poly-vinylidene fluoride) and other porous polymers have been employed as solid capillary supports. A number of self-contained immunoassay kits using porous materials as solid phase capillary carriers of immunochemical components such as antigens, haptens, or antibodies have been described.

U.S. Pat. No. 5,073,484 filed on Feb. 23, 1983 discloses a method and apparatus for the quantitative determination of an analyte in a liquid employs a liquid-permeable solid medium defining a liquid flow path. The medium includes a number of reaction-containing reaction zones spaced apart along the flow path and in which reaction occurs with the analyte or an analyte derivative (e.g., a labeled analyte) to result in the formation of a predetermined product. Detector means are employed to detect analyte, analyte derivatives, reactant or predetermined product in the reaction zones. The number of such zones in which such detection occurs indicates the amount of analyte in the liquid.

U.S. Pat. No. 6,020,147 filed on Jun. 1, 1992 discloses a device for detecting the presence of an analyte in a carrier liquid suspected of containing said analyte. The device comprises a liquid permeable solid medium which defines a path for fluid flow capable of supporting capillary flow, along which are i) a site for application of the carrier liquid, ii) a diffusively bound labeled reactant specific for the analyte or a chemical moiety which is itself the reaction product of the analyte with another chemical moiety, said labeled reactant being capable of flowing along the flow path, wherein said diffusively bound labeled reactant and said analyte or chemical moiety are of a specific ligand-receptor (antigen-antibody) pair, and iii) one or more zones spaced along said flow path, each zone having a predetermined amount of a reactant bound to it which is specific for either the analyte or a chemical moiety which is itself the reaction product of the analyte with another chemical moiety. The device can be used by contacting a carrier liquid with said application site in such a manner that permits said liquid to pass along the flow path by capillary flow such that analyte or reaction product of the analyte with another chemical moiety becomes bound to both the labeled reactant and the reactant bound to the solid medium. The labeled reactant, with the reactant bound to the solid medium, sandwiches the analyte or a chemical moiety which is itself the reaction product of the analyte with another chemical moiety.

U.S. Pat. No. 5,713,389 filed on Dec. 23, 1992 discloses a test cell for detection of a pre-selected ligand in a liquid sample such as a body fluid. The test cell includes an elongate outer casing which houses an interior permeable material capable of transporting an aqueous solution and defining a sample inlet, a test volume, and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site which includes a first protein having a binding site specific to a first epitope of the ligand immobilized in fluid communication with the flow path. The test site can be observed through a window of the casing.

U.S. Pat. No. 5,622,871 filed on Jul. 15, 1993 discloses an analytical test device useful for example in pregnancy testing, includes a hollow casing constructed of moisture-impervious solid material, such as plastics materials, containing a dry porous carrier which communicates indirectly with the exterior of the casing via a bibulous sample receiving member which protrudes from the casing such that a liquid test sample can be applied to the receiving member and permeate therefrom to the porous carrier, the carrier containing in a first zone a labelled specific binding reagent is freely mobile within the porous carrier when in the moist state, and in a second zone spatially distinct from the first zone unlabelled specific binding reagent for the same analyte which unlabelled reagent is permanently immobilized on the carrier material and is therefore not mobile in the moist state, the two zones being arranged such that liquid sample applied to the porous carrier can permeate via the first zone into the second zone, and the device incorporating an aperture in the casing, enabling the extent (if any) to which the labelled reagent becomes bound in the second zone to be observed. Preferably the device includes a removable cap for the protruding bibulous member.

U.S. Pat. No. 5,559,041 filed on Jun. 3, 1993 discloses an immunochemical assay device comprising a base member and an array disposed on the base member. The array comprises (i) a reservoir pad having sufficient porosity and volume to receive and contain a liquid sample on which the assay is to be performed; (ii) a wicking membrane disposed distally to said reservoir pad, said wicking membrane having sufficient porosity and volume to absorb a substantial proportion of the sample received in said reservoir pad; and (iii) at least one filter zone which is separate and distinct from said reservoir pad and wicking membrane, and interposed between and contiguous with said wicking membrane and said reservoir pad, said filter zone having impregnated therein a labeled immunochemical component capable of binding to an analyte of interest in said sample to form an immuno-complex, said filter zone being operable to permit passage of any specific immuno-complex to said wicking membrane while impeding passage of larger components contained in said sample. At least one immobilized substance disposed in at least one assay indicia zone of said wicking membrane downstream of said reservoir pad is operable to bind to a specific immuno-complex contained in the sample to form said assay indicia.

U.S. Pat. No. 7,109,942 filed on Feb. 12, 2001 discloses a test device for determination of an analyte in a liquid sample, comprising: (a) a nitrocellulose carrier, (b) a binding reagent effective to capture analyte, when present, in a defined detection zone of the nitrocellulose carrier; (c) a labeled reagent which is freely mobile in the nitrocellulose carrier in the presence of the liquid sample, said labeled reagent being selected such that it is captured in the detection zone when analyte is present in the liquid sample; (d) a sample receiving member; and (e) a control zone, disposed on or in the nitrocellulose carrier on a side of the detection zone remote from the sample receiving member. The control zone comprises a control binding reagent which binds the labeled reagent whether or not analyte is present in the sample. Liquid sample applied to the sample receiving member is transported to and then along the length of the nitrocellulose carrier to pass through the detection zone, and the detection of labeled reagent in the detection zone is indicative of the presence of analyte in the liquid sample.

SUMMARY OF THE INVENTION

An object of the present invention is to attain following three advantages or improvements all together at the same time: (1) to increase flow rate of blood at which the blood flows from a sample receiving pad through a conjugate pad and, thus, obtain more rapid test result; (2) to reduce a background effect in a test line and, then, improve a visual degree in the test line; and (3) to increase specific and binding amount of a binder to an analyte of interest in the blood and, thus, to improve test result quality and accuracy.

Meanwhile, needs and configurations to attain the above three advantages or improvements all together at the same time are not at all disclosed in the prior art including the above-listed US patent documents and many US patent documents which are not listed herein but were searched and reviewed by applicants of the present invention.

It is possible to attain the above-mentioned object by providing a lateral flow immunoassay device for qualitative or quantitative analysis of an analyte of interest in a whole blood sample, comprising a base member, and a horizontal array disposed on said base member. The horizontal array comprises (i) a sample receiving pad being located on one end of the base member and having pores so as to receive the whole blood sample; (ii) a conjugate pad being distinct from the sample receiving pad and being contact with the sample receiving pad and having pores and being impregnated with a diffusively bound conjugate, the conjugate pad receiving the blood from the sample receiving pad, a first immuno-complex being formed by combining the analyte in the blood and the conjugate each other in the conjugate pad, the conjugate comprising a first binder specific and binding to the analyte and a label, and the first binder being conjugated to the label; (iii) a flow delaying pad being distinct from the conjugate pad and being contact with the conjugate pad and having pores so as to receive from the conjugate pad the blood containing the analyte and the conjugate which are not yet combined each other in the conjugate pad, and the formed first immuno-complex, the flow delaying pad delaying flow of the received blood, thereby increasing the reaction time in which the non-combined analyte and conjugate are combined therein each other into a newly formed first immuno-complex; and (iv) a wicking membrane being contact with the flow delaying pad and receiving the blood from the flow delaying pad, and having an second binder which is immobilized in a test line of the wicking membrane and is specific and binding to the analyte, thereby the second binder and the first immuno-complex being combined each other to form a second immuno-complex fixed to the test line. The sample receiving pad separates a red blood cell from the whole blood sample, thereby impeding passage of the red blood cell, and a relation between average pore size (P1) of the sample receiving pad, average pore size (P2) of the conjugate pad, and average pore size (P3) of the flow delaying pad is as follows: P1>P2>P3.

In a preferred embodiment of the present invention, a polycation may be provided within and bound to the sample receiving pad in order to separate the red blood cell from the whole blood sample.

In a preferred embodiment of the present invention, the wicking membrane may further comprise a third binder which does not bind to the analyte but binds to the first binder and is immobilized in a control line of the wicking membrane, the control line being located downstream of the test line.

In a preferred embodiment of the present invention, the label may be a color particle material, a gold nanoparticle, a color-changed enzyme, or a fluorescent material.

In a preferred embodiment of the present invention, the analyte may be selected from a group consisting of an antibody, an antigen, a nucleic acid aptamer, a hapten, a antigenic protein, DNA, DNA-binding protein, a hormone, a tumor-specific marker and a tissue-specific marker. Here, the first, second and third binder may be selected from a group consisting of an antibody, an antigen, a nucleic acid aptamer, a hapten, a antigenic protein, DNA, DNA-binding protein, and a hormone-receptor.

In a preferred embodiment of the present invention, the average pore size (P3) of the flow delaying pad may be 2 to 5 µm. The average pore size (P2) of the conjugate pad may be 6 to 11 µm.

In a preferred embodiment of the present invention, the horizontal array may further comprise an absorbent pad disposed on the other end of the base member and being contact with the wicking membrane and having pores to absorb the blood from the wicking membrane.

In a preferred embodiment of the present invention, the polycation may be selected from the group consisting of poly-L-lysine hydrobromide, poly-L-arginine hydrochloride, poly-L-histidine, poly(lysine, alanine) 3:1 hydr5obromide, poly(lysine, alanine) 2:1 hydrobromide, poly(lysine, alanine) 1:1 hydrobromide, poly(lysine, tryptophan) 1:4 hydrobromide, and poly(diallyldimethylammonium chloride).

In a preferred embodiment of the present invention, the flow delaying pad may be made of a polyvinyl alcohol-bound glass fiber.

In a preferred embodiment of the present invention, the first binder may be specific to a first epitope or a first ligand of the analyte and the second binder may be specific to a second epitope or a second ligand of the analyte.

BRIEF DESCRIPTION OF THE DRAWINGS

For a more complete understanding of the present invention and the advantages thereof, reference is now made to the following description taken in conjunction with the accompanying drawings.

DETAILED DESCRIPTION OF EXEMPLARY EMBODIMENTS

Exemplary embodiments of the invention will be described below in detail with reference to the accompanying drawings.

Figure 1:
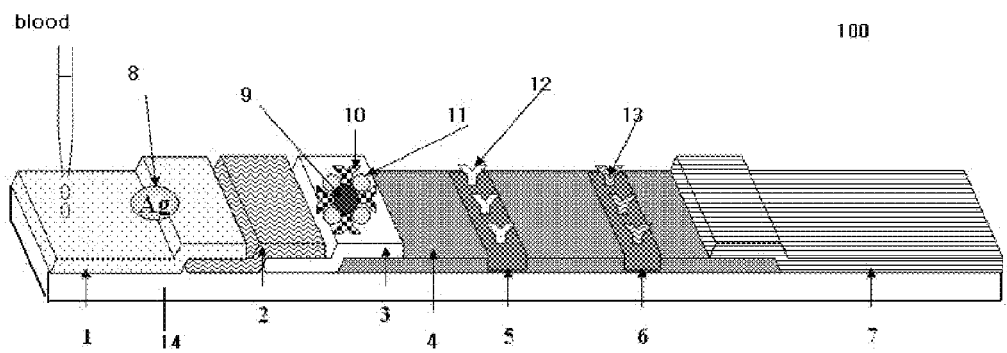
FIG. 1 is a perspective view of a lateral flow immunoassay device according to the present invention.

FIG. 1 is a perspective view of a lateral flow immunoassay device 100 according to the present invention. In this example, for colorization of immunochromatographic assay, a colored particulate material is used as a label 9. On the other hand, a color-changed enzyme or a fluorescent material may be used as the label 9. Specifically, a gold nanoparticle is used as the label 9 in this example. A test sample is a whole blood sample containing an analyte of interest (in this example, the analyte is indicated as a reference number 8 and, to be specific, is an antigen) and red blood cells, etc. In present specifications, "analyte" or "analyte of interest" refers to the compound or the composition to be detected or measured, which has at least one epitope or binding site. The analyte 8 can be any substance for which there exists a naturally occurring analyte-specific binding member or for which an analyte-specific binding member can be prepared. Analytes 8 include, but are not limited to, toxins, organic compounds, proteins, peptides, microorganisms, amino acids, nucleic acids, hormones, steroids, vitamins, drugs (including those administered for therapeutic purposes as well as those administered for illicit purposes), and metabolites of or antibodies to any of the above substances. The term "analyte" 8 also includes any antigenic substances, haptens, antibodies, macromolecules and combinations thereof.

A sample receiving pad 1 having sufficient porosity and volume to receive and contain the blood sample on which the assay is to be performed is provided on one end (in this example, left end) of a base member 14 made of a thin plastic. The sample receiving pad 1 being located on one end of the base member and having pores receives the whole blood. The sample receiving pad is made of any suitable porous and absorbent material. Such a material includes paper (fibrous), or membranes (micro porous) of cellulose materials such as paper; cellulose and cellulose derivatives such as cellulose acetate and nitrocellulose; fiber glass; cloth, both naturally occurring (e.g. cotton) and synthetic (e.g. nylon); porous gels; and the like.

Meanwhile, the red blood cells interfere with many diagnostic determinations. In assays for an analyte, red blood cells may inhibit binding between specific binding pair members. Further, in a rapid test format using a chromatography assay device, particularly a chromatography immunoassay device, red blood cells may inhibit fluid flow which is necessary for reactions to occur on the device. Moreover, the red blood cells cause a background effect around a test line 5 of the wicking membrane 4 to deteriorate a test result quality. For these reason and others, many assay methodologies are carried out on red blood cells which must first be separated from a whole blood sample.

To reduce or eliminate the need for centrifugation, assay devices have been developed which employ gradient membranes or trapping membranes to separate red blood cells from the liquid portion of the blood. Immobilized anti-red blood cell antibodies have also been used. Other known techniques for separating red blood cells from plasma or serum include (a) combining a whole blood sample with a red blood cell binding agent filtering the mixture through a solid bibulous element to which is bound at least one specific binding pair member to remove the agglutinated red blood cells; (b) passing whole blood through a glass micro fiber filter which may or may not have an agglutinating agent incorporated; (c) employing a barrier or exclusion layer of polysaccharide material to prevent red blood cells from passing through and interfering with detection or visualization of a signal on a dry test strip; and (d) using a support having a poly cationic surface which binds red blood cells but not plasma.

In order to attain the above-mentioned following two advantages or improvements all together at the same time: (1) to increase flow of the blood at which the blood flows from the sample receiving pad 1 through a conjugate pad 2 and, thus, obtain more rapid test result; and (2) to reduce a background effect in a test line 5 and then improve a visual degree in the test line 5, the present invention is characterized in that a average pore size (P1) of the sample receiving pad 1 is much larger than a average pore size (P2) of the conjugate pad 2 and a average pore size (P3) of the flow delaying pad 3, the conjugate pad 2 and the flow delaying pad 3 being located downstream of the sample receiving pad 1, and, at the same time, one of the above-mentioned red blood cell separating techniques is used in order to separate the red blood cells from the whole blood sample.

Such a configuration is to be considered in details. To increase flow of the blood at which the blood flows from the sample receiving pad 1 through the conjugate pad 2 and, thus, obtain more rapid test, a average pore size (P1) of the sample receiving pad 1 is much larger than a average pore size (P2) of the conjugate pad 2 and a average pore size (P3) of the flow delaying pad 3. However, if average pore size (P1) of the sample receiving pad 3 which receives the blood is much larger, the red blood cells can pass through the sample receiving pad and, thus, the sample receiving pad 1 can not impede the passage of the red blood cells, so that the red blood cells may inhibit binding between specific binding pair members in the conjugate pad 2 and the red blood cells may cause the background effect around the test line 5 of the wicking membrane 4 to deteriorate the test result quality and accuracy. Accordingly, in the present invention, although the pore size of the sample receiving pad 3 which receives the blood becomes much larger, the sample receiving pad 3 can impede the passage of the red blood cells by using one of the above-mentioned red blood cell separating techniques. Especially, it is preferable to provide a polycation within the sample receiving pad 1 in order that the red blood cell might be removed from the blood sample. Therefore, the more rapid test due to the rapid absorption and flow of the blood sample and the more accurate test due to the removal of the red blood cells could be attained all together at the same time.

To be specific, a red blood cell separating agent being charged positively is bound to sample receiving pad 1. Thus, it causes aggregation of the red blood cells as soon as they are applied to the sample receiving pad 1 resulting in minimal, if any, interference in the flow of the serum or plasma along a horizontal array of the sample receiving pad 1, the conjugate pad 2, the flow delaying pad 3 and wicking membrane 4 by solvent flow and capillary actions. The red blood cell separating agent of the present invention may be any substance capable of aggregating red blood cells. Preferred agents are positively charged materials such as polycations, including e.g., poly-L-lysine hydrobromide; poly(dimethyl diallyl ammonium) chloride (Merquat®-100, Merquat® 280, Merquat® 550); poly-L-arginine hydrochloride; poly-L-histidine; poly(4-vinylpyridine), poly(4-vinylpyridine) hydrochloride; poly(4-vinylpyridine)cross-linked, methylchloride quaternary salt; poly(4-vinylpyridine-co-styrene); poly(4-vinylpyridinium poly(hydrogen fluoride)); poly(4-vinylpyridinium-P-toluene sulfonate); poly(4-vinylpyridinium-tribromide); poly(4-vinylpyrrolidone-co-2-dimethylaminoethyl methacrylate); poly vinylpyrrolidone, cross-linked; poly vinylpyrrolidone, poly(melamine-co-formaldehyde); partially methylated; hexadimethrine bromide; poly(Glu, Lys) 1:4 hydrobromide; poly(Lys, Ala) 3:1 hydrobromide; poly(Lys, Ala) 2:1 hydrobromide; poly-L-lysine succinylated; poly(Lys, Ala) 1:1 hydrobromide; and poly(Lys, Trp) 1:4 hydrobromide. The most preferred polycation is poly(dimethyl diallyl ammonium) chloride (Merquat®-100). The red blood cell separating agent of the present invention may be used in any suitable amount which functions to separate the red blood cells from the rest of the sample. Preferably, the red blood cell separating agent may be present in a concentration of from about 0.04% to about 1.3% (weight per volume), with from about 0.13% to about 0.33% (weight per volume) being more preferred, and about 0.20% to about 0.33% (weight per volume) being most preferred.

The conjugate pad 2 being distinct from the sample receiving pad 1 and being contact with the sample receiving pad 1 and having pores and being impregnated with a diffusively bound conjugate is installed downstream of the sample receiving pad 1. The conjugate comprises a first binder 10 specific and binding to the analyte 8 and a label 9. The conjugate pad 2 receives from the sample receiving pad 1 the blood from which the red blood cell is removed and form a first immuno-complex by combining the analyte 8 in the blood and the conjugate each other. The first binder 10 is conjugated to the label 9 in the conjugate pad 2. As abovementioned, the label 9 may be a gold nanoparticle in this example. Moreover, in this example, a blocking agent 11 whose example is BSA (bovine serum albumin) is filled into a space between the first binders 10 and the gold particle 9 and binds to the gold particle 9. The blocking agent 11 inhibits a non-targeted or non-desired substance except the analyte 8 from binding to the gold particle 9. For example, the gold nanoparticle 9 has light absorbance rate of approximately 510 to 540 nm.

"Conjugate" refers to a substance comprising a detectable label attached to a specific binding member. The attachment may be covalent or non-covalent binding, and may include nucleic acid hybridization. The label allows the labeled substance to produce a detectable signal that is directly or indirectly related to the amount of analyte 8 in a test sample. The specific binding member component of the labeled substance is selected to bind directly or indirectly to the analyte. In this example, the label is gold particle 9. "Specific binding member" or "binder" refers to a member of a specific binding pair, i.e. two different molecules wherein one of the molecules specifically binds to the second molecule through chemical or physical means. If the specific binding member is an immuno reactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. Specific examples of specific binding members include biotin and avidin, an antibody and its corresponding antigen (both having no relation to a sample to be assayed), a single stranded nucleic acid and its complement, and the like.

Figure 2:
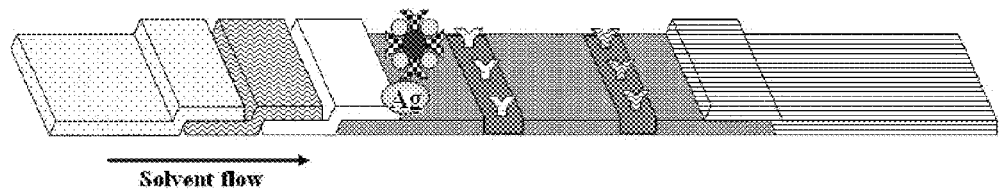
FIG. 2 is a perspective view of solvent flow in colorization of immunoassay according to the present invention.

As indicated in FIG. 2, the conjugate where the gold nanoparticle 9 is conjugated with the first binders 10 binds to the analyte 8. In FIG. 2, although the reference numbers of the components are omitted, the reference numbers of that of the FIG. 2 is identical with that of the FIG. 1. Meanwhile, when the analyte 8 is PSA (Prostate-specific antigen), the first binder 10 is a first antibody specific to a first epitope of the PSA. When the analyte 8 as an antigen is Thyroid-stimulating hormone (also known as TSH or thyrotropin), the first binder 10 is a first antibody specific to a first epitope of the TSH. When the analyte 8 as an antigen is a polypeptide consisting of amino acids 1-76 of the N-terminal of human pro-brain natriuretic factor (BNP(1-76)(SEQ ID NO:1)), the first binder 10 is a first antibody specific to a first epitope of the polypeptide consisting of amino acids 1-76 of the N-terminal of human pro-brain natriuretic factor (BNP(1-76)(SEQ ID NO:1)). When the analyte 8 is Creatine Kinase MB (CK-MB), the first binder 10 is a first antibody specific to a first epitope of the CK-MB. When the analyte 8 is Cardiac Troponin I (cTnT), the first binder 10 is a first antibody specific to a first epitope of the Cardiac Troponin I. When the analyte 8 is Myoglobin (MYO), the first binder 10 is a first epitope of the MYO. When the analyte 8 is carcinoembryonic antigen, the first binder 10 is a first antibody to specific to a first epitope of carcinoembryonic antigen. The analyte may include cancer-specific markers and tissue-specific markers.

It should be noted that in the conjugate pad 2, all the analytes 8 do not bind to the first binders 10 of the conjugate. That is to say, there remain the analytes which do not bind to the first binders 10. Accordingly, there exists need to increase the specific and binding amount of the binder to the analyte of interest in the blood and, thus, to improve test quality result and detection sensitivity. To this end, the present invention is characterized in that the flow delaying pad 3 being distinct from the conjugate pad 2 and being contact with the conjugate pad 2 and having pores receives from the pad 2 the blood containing the analyte and the conjugate which are not yet combined each other in the conjugate pad 2 and the existing formed first immuno-complex, and delays flow of the blood, thereby increasing the reaction time in which the non-combined analyte and conjugate are combined in the pad 3 each other into a newly formed first immuno-complex. Hence, the amount of resulting formed first immuno-complex which will later react to the second binder 12 in the test line 5 must increase, so that a sensitivity of detection signal in the test line 5 might be strong. In the present invention, in order to delay the flow of the blood and, in turn, increase the reaction time, a relation between average pore sizes (P2) of the conjugate pad 2 and average pore size (P3) of the flow delaying pad 3 is as follows: P2>P3, the flow delaying pad 3 being located downstream of the conjugate pad 2. That is to say, the smaller the average pore size becomes, the lower the flow rate of the blood becomes, so that the reaction time may increase and, hence, the amount of the resulting first immuno-complex may increase.

Considering the configurations which are set forth so far, the above-mentioned following three advantages or improvements: (1) to increase flow rate of the blood at which the blood flows from the sample receiving pad 1 through a conjugate pad 2 and, thus, obtain more rapid test result; (2) to reduce a background effect in a test line 5 and then improve a visual degree in the test line 5; and (3) to increase specific and binding amount of a binder to an analyte 8 of interest in the blood and, thus, to improve test result quality and accuracy are attained all together at the same time by characterizing the present invention in that the sample receiving pad 1 separates the red blood cell from the whole blood sample, thereby impeding passage of the red blood cell; and a relation between average pore size (P1) of the sample receiving pad 1, average pore size (P2) of the conjugate pad 2, and average pore size (P3) of the flow delaying pad 3 is as follows: P1>P2>P3.

Here, it is preferred that the average pore size of the flow delaying pad 3 is 2 to 5 μm. Moreover, it is preferred that the average pore size of the conjugate pad 2 is 6 to 11 μm. Further, it is preferred that the flow delaying pad 3 is made of a polyvinyl alcohol-bound glass fiber.

Figure 3:
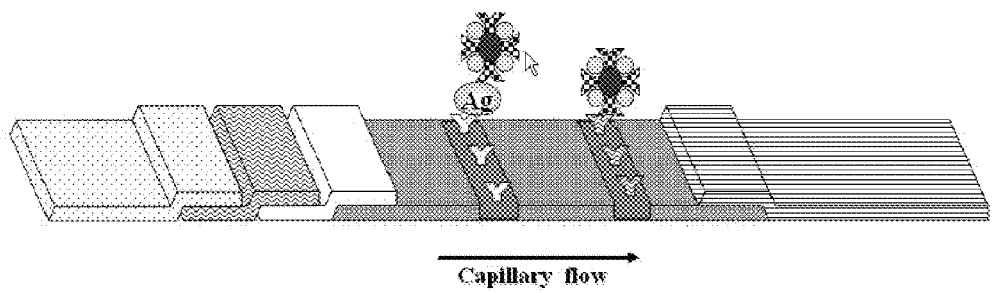
FIG. 3 is a perspective view of capillary flow in colorization of immunoassay according to the present invention.

FIG. 3 is the perspective view of capillary flow in colorization of immunoassay according to the present invention. In FIG. 3, although the reference numbers of the components are omitted, the reference numbers of that of the FIG. 3 is identical with that of the FIG. 1. The capillary flow occurs in the wicking membrane 4. The wicking membrane 4 is contact with the flow delaying pad 3 and receives the blood from the flow delaying pad 3. The wicking membrane 4 has a second binder 12 which is immobilized in the test line 5 of the wicking membrane 4 and is specific and binding to the analyte 8. Thus, the second binder 12 and the first immuno-complex are combined each other to form a second immuno-complex fixed to the test line 5, as shown in the FIG. 3. In this way, the analyte 8 is sandwiched between the first binder 11 and the second binder 12. Here, the second binder 12 is immobilized to the test line 5 and, hence, the second immuno-complex comprising the analyte 8 and the colored particles 9 is immobilized or fixed to the test line 5. In this manner, the quantity of the analyte 8 in the blood is proportional to the amount of the colored particles 9 fixed to the test line 5. Accordingly, it is possible to quantitatively measure the analytes 8 of interest in the whole blood sample by measuring the colorization level of the test line 5. For example, a CMOS camera or CDD camera is used to measure the colorization level of the test line.

In particular, as is above-mentioned, in the invention, the flow delaying pad 3 receives the blood containing the analyte 8 and the conjugate which are not yet combined each other in the conjugate pad 2 and delay the flow of the blood, thereby increasing the reaction time in which the non-combined analyte and conjugate are combined each other into the newly formed first immuno-complex. Consequently, the amount of the first immuno-complex which will bind to the second binder 12 in the test line 5 further increases and, in turn, the amount of the second immuno-complex containing the analytes 8 and the label, i.e. the colored particle 9 (in this example, gold nanoparticle) further increases. Therefore, the presence of the flow delaying pad 3 between the conjugate pad 2 and the wicking membrane 4 makes the signal level or colorization level at the test line 5 more sensitive than the absence of the flow delaying pad 3. In other words, the presence of the flow delaying pad 3 makes the test result quality on the measurement of the analyte in the blood a lot higher. Moreover, although a certain pad having pores is intervened between the conjugate pad 2 and the wicking membrane 4, the case where average pore size of conjugate pad=average pore size of the certain pad or average pore size of conjugate pad <average pore size of the certain pad forms less amount of the first immuno-complex and, hence, less sensitive signal level or colorization level than the present invention where average pore size of conjugate pad >average pore size of the certain pad (in the present invention, this certain pad is the flow delaying pad 3).

On the considerations of the second binder 12, when the analyte 8 is PSA (Prostate-specific antigen), the second binder 12 is a second antibody specific to a second epitope of the PSA. When the analyte 8 as an antigen is Thyroid-stimulating hormone (also known as TSH or thyrotropin), the second binder 12 is a second antibody specific to a second epitope of the TSH. When the analyte 8 as an antigen is a polypeptide consisting of amino acids 1-76 of the N-terminal of human pro-brain natriuretic factor (BNP(1-76)(SEQ ID NO:1)), the second binder 12 is a second antibody specific to a second epitope of the polypeptide consisting of amino acids 1-76 of the N-terminal of human pro-brain natriuretic factor (BNP(1-76)(SEQ ID NO:1)). When the analyte 8 is Creatine Kinase MB (CK-MB), the second binder 12 is a second antibody specific to a second epitope of the CK-MB. When the analyte 8 is Cardiac Troponin I (cTnT), the second binder 12 is a second antibody specific to a second epitope of the Cardiac Troponin I. When the analyte 8 is Myoglobin (MYO), the second binder 12 is a second epitope of the MYO. When the analyte 8 is carcinoembryonic antigen, the second binder 10 is a second antibody specific to a second epitope of carcinoembryonic antigen.

Subsequently, the conjugate which does not bind to the analyte 8 in the conjugate pad 2 and the flow delaying pad 3 passes by the test line 5 along with the blood. It should be appreciated that the amount of the diffusely bound conjugate comprising the label 9 and the first binder 10 within the conjugate pad 2 is much more than the amount of the analytes 8 suspected of being present in the whole blood sample. The conjugate which passes by the test line is bound to a control line 6 of the wicking membrane 4. The wicking membrane 4 further comprises a third binder 13 which does not bind to the analyte but binds to the first binder 10 and is immobilized in the control line 6 of the wicking membrane 4, the control line being located downstream of the test line. As shown in the FIG. 3, in the control line 6, the first binder 10 of the conjugate which does not bind to the analyte 8 is bound and fixed to the third binder 13 of the control line 6. In this way, the control line exists for the following two purposes. First, the control line 6 indicates that the liquid biological sample, i.e. the whole blood sample has been conveyed thereto by capillarity along the pads 1, 2, and 3, and the membrane 4 irrespective of a presence or absence of said analyte in said liquid biological sample. That is to say, the control line 6 indicates validity of the test. Second, the control line 6 indicates positive assay indicia. To be specific, if the analyte 8 is not present in the whole blood sample, the colorization will not occur in the test line 5 but in the control line 6.

Here, the third binder 13 is selected from a group consisting of an antibody, an antigen, and a hapten. Antibodies as the third binder 13 may be polyclonal or monoclonal, and are available with specificity for whole Ig molecules or antibody fragments such as the Fc or Fab regions. For example, if a colloidal gold labelled mouse anti-human IgG is used in the conjugate pad 2, the antibody at the control line 6 would be anti-mouse IgG.

Subsequently, the blood which passes by the control line 6 flows into an absorbent pad 7 disposed on the other end of the base member 14 and being contact with the wicking membrane 4 and having pores to absorb the blood from the wicking membrane 4.

Example 1

PSA (Prostate Specific Antigen) Test

A. Preparation of a Conjugate

Gold sol particles were prepared according to a procedure well known in the art such as U.S. Pat. No. 4,313,734. The pH of gold sol is adjusted to 7. Mouse anti-PSA antibody (final concentration 20 μg/ml) is added to 1 ml of gold sol solution and stirred vigorously for 30 min at ambient temperature. 0.1 ml of 10% Neo Protein Saver is added, and the solution is continuously stirred for approximately 30 min at ambient temperature. Colloidal gold-monoclonal antibody conjugate is recovered by centrifugation at 10,000 rpm in GSA rotor for 20 min, discarding the supernatant and suspending the resultant pellet in 1 ml 50 mM boric acid, pH 7.4. The suspension is then spun down at 10.000 rpm for 20 min in GSA rotor. The supernatant once again is discarded and the pellet suspended in 0.5 ml of 1% Neo Protein Saver and 1% sucrose in 50 Mm boric acid, pH 7.4.

B. Preparation of Horizontal Array on the Base Member

A double sided transparent tape is attached on the upper surface of a thin plastic plate. A piece or strip of nitrocellulose membrane with pore size of 5 μm is cut and attached directly on the top of the double sided tape. An assay indicia zone of immobilized test line for PSA is defined on the membrane by impregnating 15 ul of solution of 1 mg/ml monoclonal. PSA antibody. For a control line, 1 mg/ml of goat anti-mouse antibody is defined on the membrane downstream of the test line. After printing, the membrane is dried at ambient temperature for approximately 12 hours. The base member and wicking membrane can be stored in a desiccator until further processed. A flow delaying pad is made of a polyvinyl alcohol-bound glass fiber with an average pore size of 2 μm. The flow delaying pad is cut and attached directly on the top of the double sided tape with be contacting with the membrane. A conjugate pad is prepared by wetting a solution of colloidal gold mouse anti-PSA antibody conjugate of 3% dextran sulfate, 5% sucrose, and 2% Neo Protein Saver in 10 mM PBS (pH7.4) to rectangular piece of pretreated glass fiber with an average pore size of 11 μm. The conjugate pad is stored dry in a desiccator until use. The conjugate pad is attached directly on the top of the double sided tape with being contact with the flowing delay pad. A sample pad with an average pore size between about 30 and 150 μm is wetted with solution of 1.3% cationic polymer (poly-L-lysine hydrobromide) as a polycation in the PBS 10 mM (Phosphate buffer saline, PH 7.4) and is dried. The dried sample pad is attached directly on the top of the double sided tape with be contact with the conjugate pad.

C. Assay Result

When a pipette of 100 μl of a whole blood sample is applied to the sample receiving pad, a detectable signal begins to appear in the test line after 2 minutes 40 seconds. The assay sensitivity is 0.5 ng/mL.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

As one modification of the present invention, the wicking membrane has further another test line disposed between the test line and the control line. A fourth binder specific to a third epitope of the analyte is fixed to said another test line.

As further modification of the present invention, the analyte of interest in the whole blood sample comprises a plurality of analyte, the conjugate pad is impregnated with another diffusively bound conjugate comprising a fourth binder specific and binding to another analyte and a colored particulate material, the wicking membrane has further another test line disposed between the test line and the control line, and a fifth binder specific to said another analyte is fixed to said another test line. For example, the analyte is free PSA (prostate specific antigen) and said another analyte is complex PSA. As is well known to those skilled in the art, the complex PSA is bound to 1-antichymotrypsin while the free PSA is free from 1-antichymotrypsin.

As further modification of the present invention, a polyanion for neutralizing the polycation is further provided within and bound to the conjugate pad 2. The polyanion is selected from dextran sulfate, poly(acrylic acid), poly(sodium-4-styrene sulfonate), poly(vinyl sulfonic acid), poly(methyl methacrylic acid), poly-L-aspartic acid and carboxymethyl cellulose. The polyanion is capable of neutralizing the positive charge of the red blood cell separating agent, thereby eliminating or at least minimizing any interference to the assay system caused by the red blood cell separating agent.

What is claimed is:

1. A lateral flow immunoassay device for qualitative or quantitative analysis of an analyte of interest in a whole blood sample, the device comprising:
   a base member; and
   a horizontal array disposed on said base member, the horizontal array comprising:
   (i) a sample receiving pad
      being located on one end of the base member,
      having pores having an average pore size of 30 to 150 micrometers, which receive a whole blood sample, and
      which comprises a polycation which separates a red blood cell from the whole blood sample, thereby impeding passage of the red blood cell;
   (ii) a conjugate pad
      being distinct from the sample receiving pad,
      being in contact with the sample receiving pad,
      having pores having an average pore size of 6 to 11 micrometers, and
      comprising a diffusively bound conjugate, which forms a first immuno-complex with an analyte of the blood in the conjugate pad, the conjugate comprising
      a first binder specific to the analyte, and
      a label;
   (iii) a flow delaying pad
      being distinct from the conjugate pad,
      being in contact with the conjugate pad,
      having pores having an average pore size of 2 to 5 micrometers, and
      which receives from the conjugate pad the blood containing the analyte and the conjugate which are not yet combined each other, and the first immuno-complex; and
   (iv) a wicking membrane
      being in contact with the flow delaying pad, and
      having a second binder, which is immobilized in a test line of the wicking membrane, is specific to the analyte, and which combines with the first immuno-complex to form a second immuno-complex fixed to the test line, and
      which receives the blood from the flow delaying pad; and
   wherein a relation between average pore size (P1) of the sample receiving pad, average pore size (P2) of the conjugate pad, and average pore size (P3) of the flow delaying pad is as follows: P1>P2>P3.

2. The device of claim 1, wherein the wicking membrane further comprises a third binder which does not bind to the analyte but binds to the first binder and is immobilized in a control line of the wicking membrane, the control line being located downstream of the test line.

3. The device of claim 1, wherein the label is a color particle material, a gold nanoparticle, a color-changed enzyme, or a fluorescent material.

4. The device of claim 1, wherein the analyte is selected from a group consisting of an antibody, an antigen, a nucleic acid aptamer, a hapten, a antigenic protein, DNA, DNA-binding protein, a hormone, a tumor-specific marker and a tissue-specific marker.

5. The device of claim 4, wherein the first, second and third binder are selected from a group consisting of an antibody, an antigen, a nucleic acid aptamer, a hapten, a antigenic protein, DNA, DNA-binding protein, and a hormone-receptor.

6. The device of claim 1, wherein said horizontal array further comprises an absorbent pad disposed on the other end of the base member and being contact with the wicking membrane and having pores to absorb the blood from the wicking membrane.

7. The device of claim 1, wherein said polycation is selected from the group consisting of poly-L-lysine hydrobromide, poly-L-arginine hydrochloride, poly-L-histidine, poly(lysine, alanine) 3:1 hydr5obromide, poly(lysine, alanine) 2:1 hydrobromide, poly(lysine, alanine) 1:1 hydrobromide, poly(lysine, tryptophan) 1:4 hydrobromide, and poly(diallyldimethylammonium chloride).

8. The device of claim 1, wherein the flow delaying pad is made of a polyvinyl alcohol-bound glass fiber.

9. The device of claim 5, wherein the first binder is specific to a first epitope or a first ligand of the analyte and the second binder is specific to a second epitope or a second ligand of the analyte.

10. The device of claim 1, wherein a polyanion for neutralizing the polycation is further provided within and bound to the conjugate pad.

11. The device of claim 10, wherein the polyanion is selected from dextran sulfate, poly(acrylic acid), poly(sodium-4-styrene sulfonate), poly(vinyl sulfonic acid), poly(methyl methacrylic acid), poly-L-aspartic acid and carboxymethyl cellulose.

* * * * *